United States Patent [19]

Bender

[11] Patent Number: 5,262,653
[45] Date of Patent: Nov. 16, 1993

[54] SCANNER FOR NAPLESS AREAS ON A WEB HAVING BEAMS TRAINED TANGENTIALLY THEREON

[75] Inventor: Dieter Bender, Ochtrup, Fed. Rep. of Germany

[73] Assignee: Carl Schmale GmbH & Co. KG, Ochtrup, Fed. Rep. of Germany

[21] Appl. No.: 777,563

[22] PCT Filed: Jun. 2, 1990

[86] PCT No.: PCT/DE90/00430

§ 371 Date: Dec. 3, 1991

§ 102(e) Date: Dec. 3, 1991

[87] PCT Pub. No.: WO90/15896

PCT Pub. Date: Dec. 27, 1990

[30] Foreign Application Priority Data

Jun. 22, 1989 [DE] Fed. Rep. of Germany ....... 8907659

[51] Int. Cl.⁵ .................................................. G01N 21/86
[52] U.S. Cl. ...................................... 250/571; 26/51.5; 26/70
[58] Field of Search ................... 250/572, 560, 571; 356/238, 429; 28/159, 162; 26/51.5, 70, 29 R

[56] References Cited

U.S. PATENT DOCUMENTS 2,707,815  5/1955  Hadley ............................... 26/29 R
5,043,590  8/1991  Strandberg, Jr. et al. .......... 356/429

Primary Examiner—David C. Nelms
Assistant Examiner—Que T. Le
Attorney, Agent, or Firm—Herbert Dubno

[57] ABSTRACT

In order to provide a device for the lateral scanning of napless areas of fabric webs which operates automatically with great accuracy and reliability even at high web speeds while being of relatively simple construction, it is proposed to cause the fabric web (7) to pass over a guide roller (11) and to cause the napless areas (9, 12) of the fabric web (7) to be scanned by means of photodetectors (2-6) consisting of transmitters and receivers, in which the scanning beams are directed tangentially to the guide roller (11) and thus to the fabric web (7) at its deflection point.

2 Claims, 2 Drawing Sheets

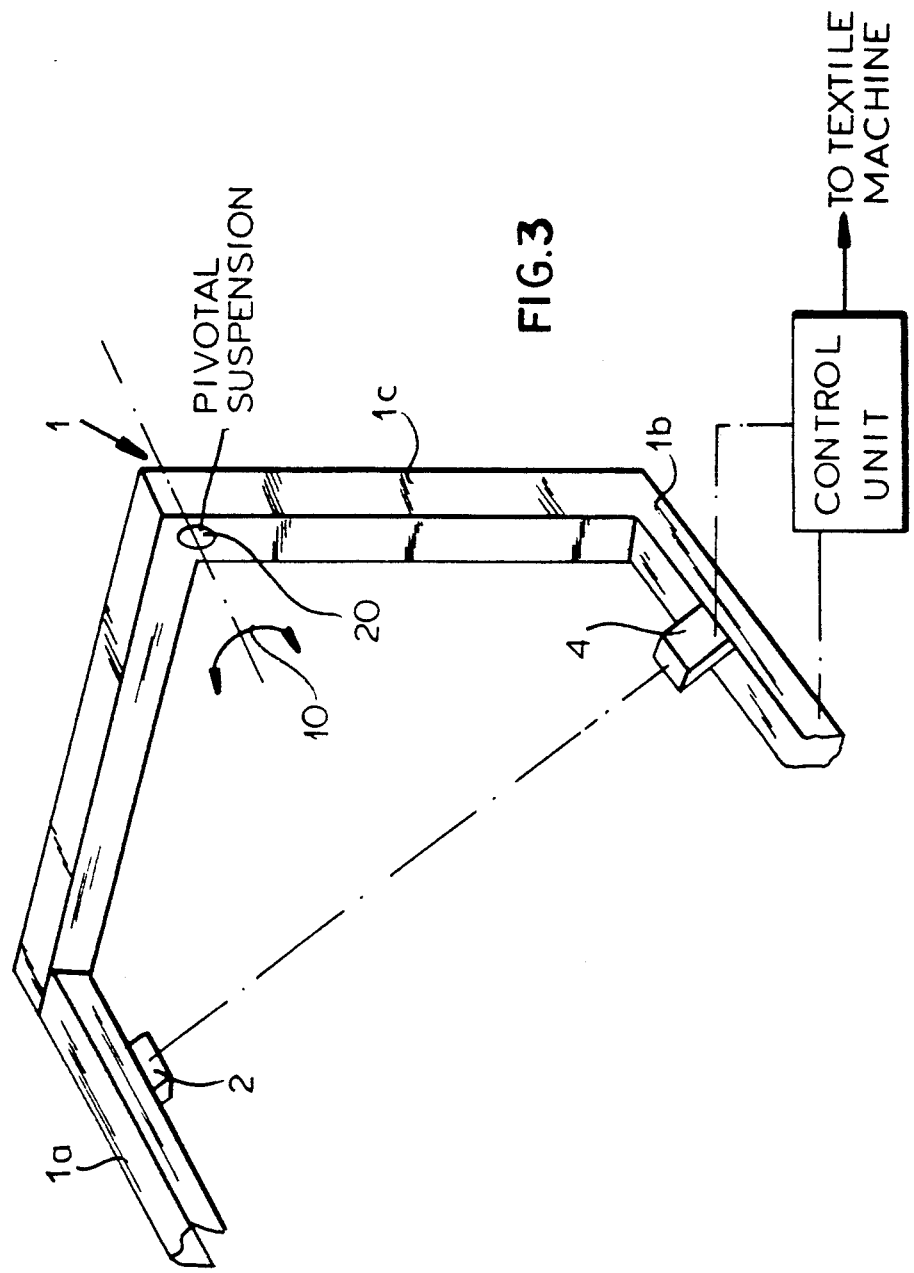

SCANNER FOR NAPLESS AREAS ON A WEB HAVING BEAMS TRAINED TANGENTIALLY THEREON

CROSS REFERENCE TO RELATED APPLICATIONS

This application is a National Phase of PCT/DE 90/00430 filed 2 June 1990 and based, in turn, upon German national application G 89 07 659.1 filed 22 June 1989 under the International Convention.

FIELD OF THE INVENTION

The invention relates to a device for the lateral scanning of napless areas on fabric webs, particularly terry cloth, in a textile machine.

BACKGROUND OF THE INVENTION

In the processing especially of terry cloth in automatic sewing installations, such as crosscutting machines, there are numerous ways of scanning the napless zones along which the cross cutting is to be affected. The known solutions work with vertically adjustable bars (e.g. German Patent 30 24 389) or with alignment beams (e.g. German open application 36 24 994), which in addition also prepare the napless stretch so that the cross-cutting takes place between the weft yarns.

Also, the lateral napless edges along a fabric web have also been scanned by means of mechanical sensors. Thereby difficulties have arisen, particularly in fast-running webs, leading to disturbances.

However, a device which can be used in textile machines for the lateral scanning of napless areas, such as particularly found in terry cloth, which proves satisfactory in all applications has not been found prior to the invention.

OBJECTS OF THE INVENTION

It is an object of the invention to provide a device for the lateral scanning of napless areas in fabric webs, which operates automatically with high precision and reliability even at high web speeds and which has a relatively simple construction.

Another object is to provide a device for the purposes described which avoids drawbacks of the prior art units.

SUMMARY OF THE INVENTION

The device for the lateral scanning of napless areas on fabric webs, particularly terry cloth, in a textile machine, of the invention is characterized in that within the range of the scanning device the fabric web runs over a guide roller; and the scanning of the napless zones of the fabric web is performed by means of photodetectors, consisting of transmitters and receivers, whereby the scanning beams are directed tangentially to the guide roller and thereby to the fabric web at its deflection point.

The transmitters and the receivers can be mounted on a frame, so that on one side the two transmitters are arranged and on a second side the receivers are arranged, whereby one transmitter with its receivers serve for scanning the nap edge of the napless area and the other transmitter with its receiver serve for scanning the edge of the napless area running across the fabric web.

Advantageously the frame is pivotable.

The first transmitter can emit a fan-shaped signal which is received either only by one of its receivers, by both of its receivers or by none of the receivers, depending on the position of the nap edge of the napless area along the fabric web.

The three possible signals can be evaluated in a control unit which actuates an adjusting element of the textile machine.

The second transmitter and the receiver in the area of the napless zone are in contact with each other and thereby interrupt the scanning of the nap edge.

The device of the invention operates as an optical nap scanner and is characterized by a very simple construction, whereby a high degree of reliability is achieved.

The installation operates virtually maintenance free and with relatively little expense. The signals obtained through the device are evaluated in the available machine control.

BRIEF DESCRIPTION OF THE DRAWING

The above and other objects, features, and advantages will become more readily apparent from the following, reference being made to the accompanying drawing in which:

FIG. 3 is a perspective view of a portion of the frame of the device.

SPECIFIC DESCRIPTION

Figure 2:
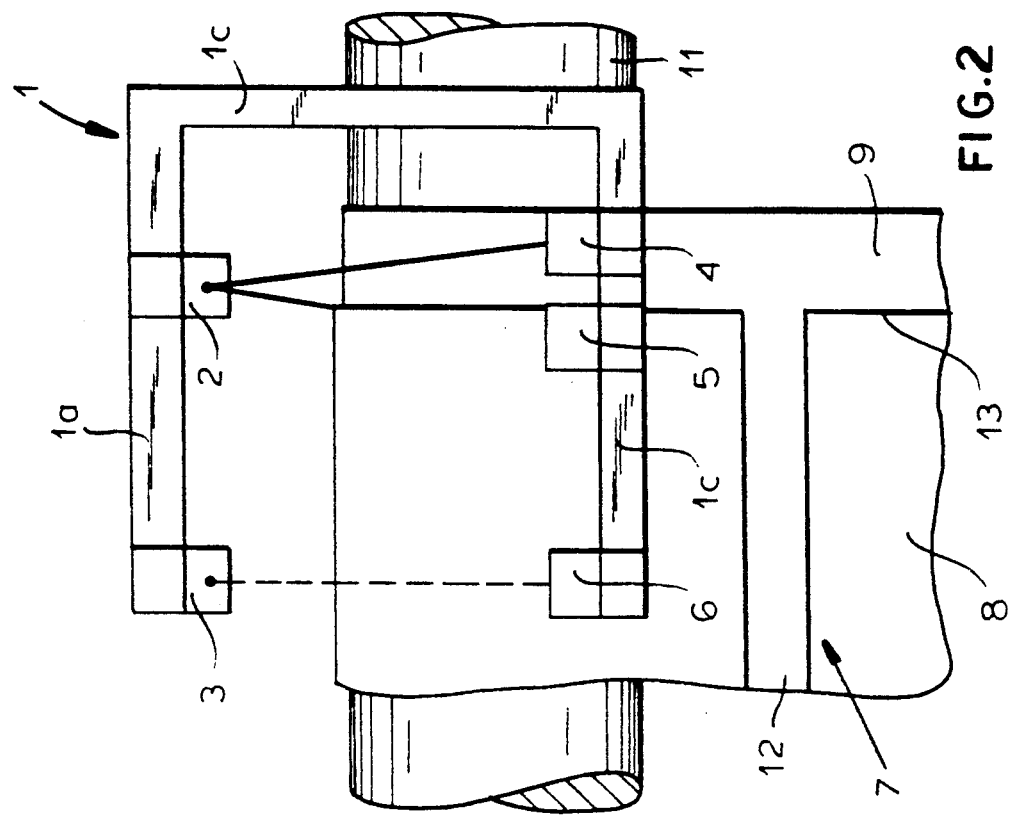
FIG. 2 view of the device according to FIG. 1 seen in the direction of arrow 14 of FIG. 1.
Figure 1:
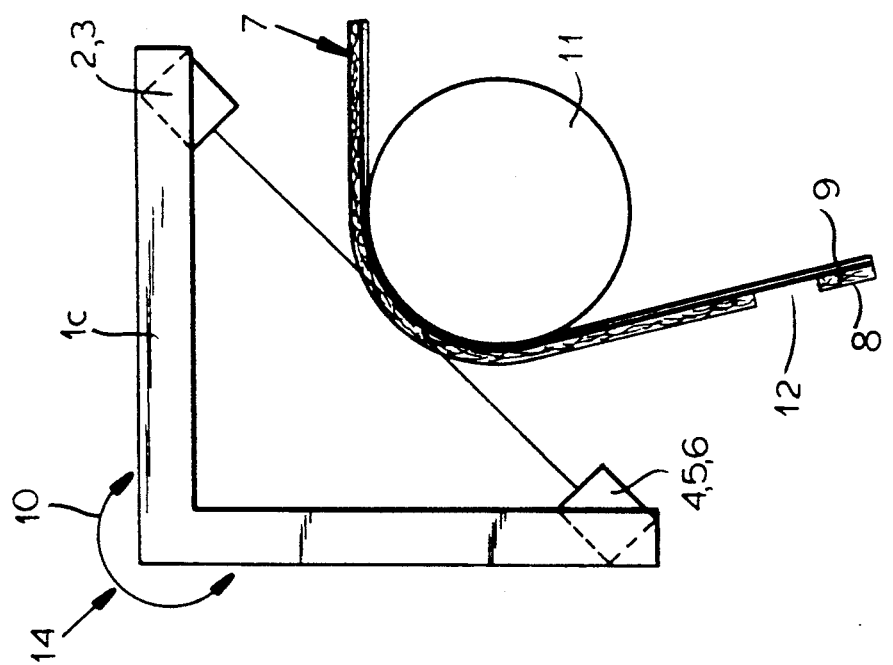
FIG. 1 is a side view transverse to the running direction of the fabric web illustrating a device according to the invention.

FIGS. 1-3 show the fabric web 7 guided around a guide roller 11. The fabric web 7, e.g. a web of terry cloth, contains napless areas 9, 12 between the pile zones 8. The deflection of the fabric web 7 over the roller 11 takes place at angle preferably less than 90°, so that a tangent can intercept the napless areas 9 or 12.

The scanning of the napless area 9, i.e. the napless area running laterally along the edge of the fabric web 7, is performed by photodetectors 2-6, consisting of transmitters and receivers mounted on a frame 1. On one side 1a of the frame 1 the transmitters 2, 3 are mounted and the receivers 4-6 are mounted on side 1b. The transmitter 2 cooperates with the receivers 4, 5 on the side 1b in the scanning of the nap edge 13 of the napless area 9, while the transmitter 3 cooperates with the receiver 6 in detecting the edge of the napless area 12 running across the fabric web 7 when that edge intercepts the beam from the transmitter 3.

The frame 1 is pivotable in the direction of arrow 10 around an axis running through the connection 1c of the two sides 1a, 1b.

Furthermore, the frame 1 is movable in the direction of arrow 14 and in a direction contrary to arrow 14. This way, the sensitivity of the device is adjustable. When the frame 1 is swung in the direction of arrow 10 on the pivotal suspension 20, the distance between the transmitter 2 and the scanning point is changed, changing also the breadth of the signal, which as shown in FIG. 1 is fan-shaped. The breadth of the fan-shaped signal at the scanning point is a measure of the sensitivity of the device.

The adjustment possibilities are also a necessity for the adjustment of the device to various thicknesses of the fabric web.

As shown in FIG. 1, the transmitter 2 emits a fan-shaped signal which is received only by receiver 4, by the receivers 4, 5 together or by none of the receivers 4, 5, depending on the position of the nap edge 13 of the napless area 9 along the fabric web 7. Each of the three possible signals is evaluated in a control unit available in the textile machine and which actuates an adjusting element of the machine.

When the transmitter 3 and the receiver 6 within the range of the napless zone 12 are in communication with one another, through the beam, the scanning of the nap edge 13 of the napless zone 9 is interrupted.

I claim:

1. A device for scanning a fabric web for napless zones extending respectively longitudinally and transversely of the web, said device comprising:
    a guide roller deflecting said web through an arc around said guide roller;
    an angularly shaped frame having a pair of opposite sides;
    a first transmitter on one of said sides training a first scanner beam substantially tangentially to said web at a location at which said web extends around said roller and in a position for said scanner beam to be intercepted by an edge of said napless zone extending longitudinally of said web;
    two receivers for said first scanner beam disposed on the other of said sides opposite said first transmitter and spaced apart along said other of said sides for signalling a position of said edge;
    a second transmitter on said one of said sides spaced from said first transmitter and training a second scanner beam substantially tangentially to said web at a location at which said web extends around said roller and in a position for said second scanner beam to be intercepted by nap of said web flanking the napless zone extending transversely of the web;
    a third receiver disposed on said other of said sides opposite said second transmitter and spaced from said two receivers for receiving said second scanner beam and signalling sensing of said napless zone extending transversely of the web; and
    means for pivotally suspending said frame for adjustment of distances of said sides from said roller.

2. The device defined in claim 1 wherein said frame has two arms adjoining at a connection point and approximately perpendicular to one another, said sides extending parallel to one another and being cantilevered from respective free ends of said arms, said means for pivotally suspending said frame including means defining a pivot axis running substantially through said connection point.

* * * * *